United States Patent
Ho et al.

(10) Patent No.: US 7,091,378 B2
(45) Date of Patent: Aug. 15, 2006

(54) PREPARATION OF HYDROXAMIC ACIDS FROM ESTERS IN SOLUTION AND ON THE SOLID PHASE

(75) Inventors: Chih Yung Ho, Lansdale, PA (US); Eric David Strobel, Warrington, PA (US)

(73) Assignee: Janssen Pharmaceutica, N.V., Beerse (BE)

( * ) Notice: Subject to any disclaimer, the term of this patent is extended or adjusted under 35 U.S.C. 154(b) by 0 days.

(21) Appl. No.: 10/885,277

(22) Filed: Jul. 6, 2004

(65) Prior Publication Data

US 2006/0009658 A1    Jan. 12, 2006

(51) Int. Cl.
C07C 259/06    (2006.01)
C07C 259/08    (2006.01)
C07C 259/10    (2006.01)

(52) U.S. Cl. ............... 562/621; 562/622; 562/623; 546/141; 548/491

(58) Field of Classification Search ............... 560/621, 560/622, 623; 546/141; 548/491
See application file for complete search history.

(56) References Cited

OTHER PUBLICATIONS

Appelt, K., Eds. Hydroxamic Acid Matrix Metalloproteinase Inhibitors, Humana Press; Totowa, NJ 2000; pp. 113-142.
Barlaan, Bernard, et al. "Solid-phase Synthesis of Hydroxamic Acid Based TNF-α Convertase Inhibitors", Tetrahedron 1999, 55, 7221-7232.
Bauer, Udo, et al. "A Novel Linkage for the Solid-Phase Synthesis of Hydroxamic Acids", Tetrahedron Letters 1997, 72332-7236.
Burns, C. J., et al. Angew. Chem. Int. Ed 1998, 37, pp. 2848-2850.
Chen, Shui-Tein, et al. "One-Pot Synthesis of Cathepsin Ihhibitors: Nα-Protected N-Peptidyl-O-Acetyl Hydroxlyamines Catalysed by Alcalase Followed by Lipase in Anhydrous t-Butanol", Bioorg. Med. Chem. Letters 1992, 2, 1685-1690.
Dankwardt, Sharon M., et al. "Solid-Phase Synthesis of Di-and Tripeptidic Hydroxamic Acids as Inhibitors of Procollagen C-Proteinase", Bioorg. Med. Chem. Letters 2000, 10, 2513-2516.
Dankwardt, Sharon M., "Solid Phase Synthesis of Hydroxamic Acids", Roche Bioscience, Synlett, Jul. 1998; p. 761.
Ede, Nicholas J., et al. "Synthesis of Hydroxamic Acids Using SynPhase Crowns: Development of the Hydroxylamine Trityl linker", Letters in Peptide Science 6; 1999, pp. 157-163.
Fingleton, Barbara "Matrix Metalloproteinase Inhibitors for Cancer Therapy: The Current Situation and Future Propsects", Expert Opino. Ther. Targaets (2003), 7(3) 385-397.
Floyd, Christopher D., et al. "A Method for the Synthesis of Hydroxamic Acids on Solid Phase", Tetrahedron Letters 1996, 37, 8045-8048.
Hauser, C. R., et al. "Benzohydroxamic Acid", Org. Syn. Coll. Vol. 2, 1943, 67068.
Hogberg, Thomas et al. "Cyanide as an Efficient and Mild Catalyst in the Aminolysis of Esters", J. Org. Chem. 1987, 52, 2033-2036.
Mellor, Sarah L. et al., "N-Fmoc-Aminooxy-2-Chlorotrityl Polystrene Resin: A facile Solid-Phase Methodology for the Synthesis of Hydroxamic Acids", Tetrahedron Letters 1997, 38, 3311-3314.
Mori, K. et al., "Synthesis of Trichostatin A. A Potent Differentiation Inducer of Friend Leukemic Cells and Its Antipode", Tetrahedron Letters 1988, 44, 6013-6020.
Ngu, K., et al. "A New and Efficient Solid Phase Synthesis of Hydroxamic Acids", J. Org. Chem, 1997, 62, 7088-7080.
Salvino, Joseph M., et al. "Solid-Phase Synthesis of an Arylsulfone Hydroxamate Library", Bioorg. Med. Chem. Lett. 2000, 10, 1637-1640.
Spengler, Jan, et al. Synthesis 1998, I, 67-70.
Thouin E., et al. "Effective Synthesis of Enantiopure Hydroxamates by Displacement of Resin-Bound Esters with Hydroxylamine", Tetrahedron Letters 2000, 457-469.
Zhang, Wei, et al. "Solid-Phase Synthesis of C-Terminal Peptide Hyroxamic Acids", J. Comb. Chem. 2001, 3, 151-153.

*Primary Examiner*—Bernard Dentz
(74) *Attorney, Agent, or Firm*—Hal B. Woodrow

(57) ABSTRACT

The present invention provides a novel method for the formation of hydroxamic acids comprising reacting under suitable conditions an ester with hydroxylamine in the presence of cyanide anion.

8 Claims, 1 Drawing Sheet

PREPARATION OF HYDROXAMIC ACIDS FROM ESTERS IN SOLUTION AND ON THE SOLID PHASE

FIELD OF THE INVENTION

The present invention relates to a process for preparing hydroxamic acids from their corresponding esters in both the solution and solid phase. More particularly, the present invention relates to a process in which the addition of cyanide ion provides a novel method for the formation of hydroxamic acids from esters.

BACKGROUND OF THE INVENTION

Hydroxamic acid analogs are important targets in medicinal chemisty because of their bidentate chelating interaction with the catalytic $Zn^{2+}$ in the active site of metalloproteinases. (Fingleton, B. *Expert Opin. Ther. Targets* (2003), 7(3), 385–397; Clendeninn, N. J.; Appelt, K., Eds. Hydroxamic acid matrix metalloproteinase inhibitors. Humana Press: Totowa, N.J., 2000; pp. 113–142.

The direct solution-phase hydroxyamination of esters is generally achieved by a two-step methods involving 1) the potassium salt of hydroxylamine followed by the addition of the ester in alcohol solvent, Hauser, C. R.; Renfrow, W. B. *Org. Syn., Coll. Vol.* 2 1943, 67–68, or 2) saponification of the ester followed by activation of the acid and quenching with an O-protected hydroxylamine analog, Burns, C. J. et al. *Angew. Chem. Int. Ed.* 1998, 37, 2848–2850; Mori, K., et al. *Tetrahedron* 1988, 44, 6013–6020. In special cases, the hydroxyamination of esters has been achieved via enzymatic methods Chen, S-T. et al. *Bioorg. Med. Chem. Letters* 1992, 2, 1685–1690, and, for more reactive esters, by treatment with excess hydroxylamine in alcohol solvent. Spengler, J., et al. *Synthesis* 1998, 1, 67–70.

The solid-phase synthesis of hydroxamic acids via the direct cleavage of an ester-linked substrate has been reported. Dankwardt, S. M. *SYNLETT* 1998, 7, 761; Dankwardt, S. M., et al. *Bioorg. Med. Chem. Letters* 2000, 10, 2513–2516. However, this method requires exposure of the esterified resin to concentrated aqueous hydroxylamine in THF over 2 days and is limited in scope because of irreproducibility. Zhang, W., et al. *J. Comb. Chem.* 2001, 3, 151–153; Thouin, E., et al. *Tetrahedron Letters* 2000 457–460. The issue with simply using a hydroxylamine resin is that important chemistries like the Mitsunobu reaction and alkylations are problematic because of the acidic NH group (pKa~10).

Alternatives to address this include a method where ester libraries are made on-resin, cleaved and re-attached to a hydroxylamine resin then cleaved again, Salvino, J. M., et al. *Bioorg. Med. Chem. Lett.* 2000, 10, 1637–1640; and specialized resins, Barlaam, B. et al. *Tetrahedron* 1999, 55, 7221–7232; Mellor, S. L., et al. *Tetrahedron Letters* 1997, 38, 3311–3314; Floyd, C. D., et al. *Tetrahedron Letters* 1996, 37, 8045–8048; Ede, N. J., et al. *Letters Pep. Sci.* 1999, 6, 157–163; Bauer, U, et al. *Tetrahedron Letters* 1997, 7233–7236, where the hydroxylamine-linking group is fully protected. Ngu, K., et al. *J. Org. Chem.* 1997, 62, 7088–7089.

Also reported in the literature is the formation of amides from the reaction of an ester with an amine in the presence of small amounts of cyanide ion (Hogberg, T., et al. *J. Org. Chem.* 1987, 52, 2033–2036).

SUMMARY OF THE INVENTION

The present invention provides a novel method for the formation of hydroxamic acids comprising reacting under suitable conditions an ester with hydroxylamine in the presence of cyanide anion. The present invention provides an efficient conversion of esters to hydroxamic acids for the preparation of multigram quantities of compounds, and a versatile method for the preparation of compounds on the solid phase.

DETAILED DESCRIPTION OF THE INVENTION

Figure 1:
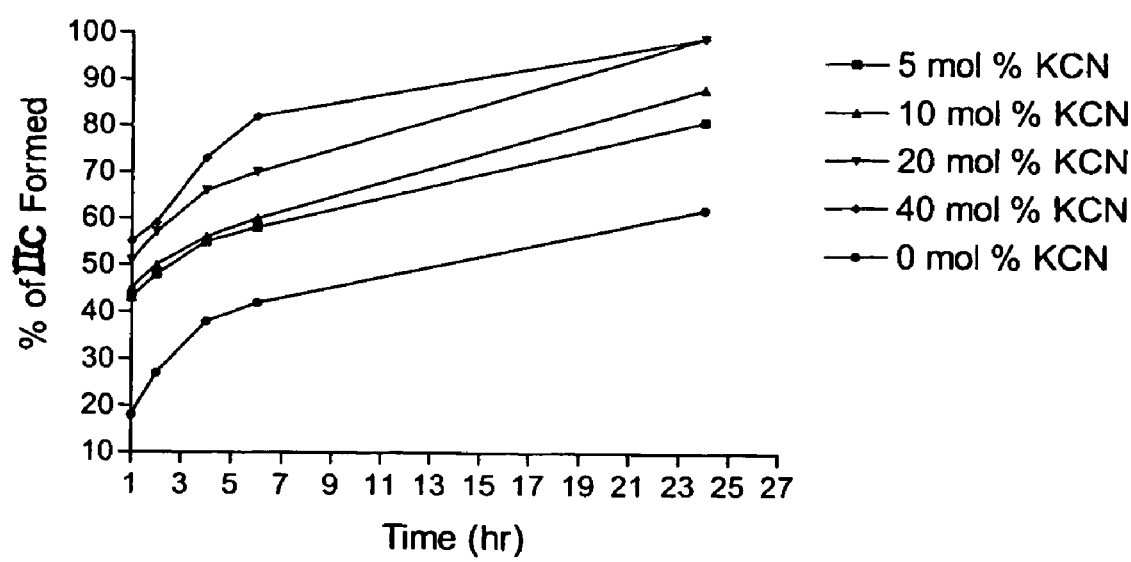
FIG. 1 depicts the effect of mole concentration of cyanide on the reaction profile for the conversion of an ester to its hydroxamic acid.

The present method improves upon the existing methods known in the art for the formation of hydroxamic acids from esters by transiently activating an ester towards the N-acylation of hydroxylamine. The present invention also extends the use of cyanide anion beyond its role in the conversion of esters to amides to encompass hydroxylamine as a reagent for both the solution and solid phase synthesis of hydroxamic acids.

Scheme 1.

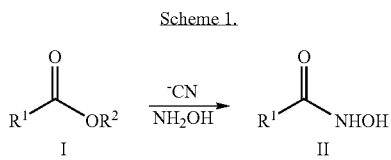

As shown in Scheme 1, an ester of Formula I, wherein $R^1$ is any organic side chain such that if the side chain includes sensitive functional groups, they are appropriately protected, and $R^2$ is $C_{1-6}$alkyl, preferably methyl, ethyl, or propyl.

Suitable conditions under which $R^1$ may be reacted with aqueous hydroxylamine, preferably from about 20 to about 80% aqueous hydroxylamine, include
in a protic solvent, preferably a $C_{1-6}$alcoholic solvent most preferably $C_{1-4}$ such as methanol or ethanol,
in which a cosolvent is optionally present, such as tetrahydrofuran, dimethylformamide, or halogen-containing hydrocarbons such as dichloromethane, chloroform and the like;
in the presence of from about 5 to about 50 mole percent, preferably from about 20 to about 40 mole percent, of a cyanide salt such as potassium cyanide, sodium cyanide, or the like;
at a temperature from about 0 to about 100° C., preferably at about 25° C.;
to form a hydroxamic acid of Formula II.

An aspect of the present invention relates to the adaptation of the reaction to the solid phase chemisty described herein, wherein $R^{2a}$ is a hydroxy-substituted resin that is activated to form ester linkages of Formula III, such as Wang resin, hydroxymethylbenzamide (HMBA-AM), HMBA-PGEG A resin, NOVASYN®TG HMBA resin, or hydroxymethylpolystyrene resin, preferably HMBA-AM.

Suitable conditions under which $R^{2a}$ may be reacted with aqueous hydroxylamine, preferably from about 20 to about 80% aqueous hydroxylamine, include in an organic solvent such as methanol, N,N-dimethylformamide (DMF), or tetrahydrofuran;

or in a mixture of organic solvents such as DMF:methanol, THF:methanol, or DMF:methanol:THF;

in the presence of from about 5 to about 50 mole percent, preferably from about 20 to about 40 mole percent, of a cyanide salt such as potassium cyanide, sodium cyanide, or the like;

at a temperature from about 0 to about 100° C., preferably at about 25° C.;

to form a hydroxamic acid of Formula IV, as shown in Scheme 2.

Scheme 2.

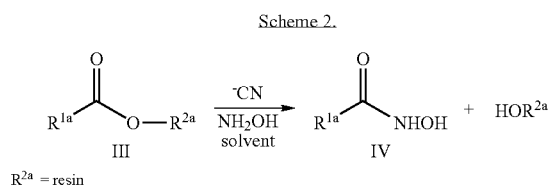

$R^{2a}$ = resin

One skilled in the art will recognize that although the instant process is suitable for forming any hydroxamic acid, esters of formula I and formula III containing additional reactive functional groups may need to be protected using reagents and methods known to those skilled in the art. See Green, T. W., Wuts, P. G. M, *Protective Groups in Organic Synthesis* (2$^{nd}$ Edition, 1991).

Reactions of the present invention may be monitored using a number of analytical methods familiar to one skilled in the art. It should be recognized that rates of reactions may be dependent upon variables such as reaction concentration, solvent, temperature, and pressure.

Those of ordinary skill in the art will recognize that reasonable variations in reagents, starting materials, concentrations and reaction conditions can be used without departing from the scope of the present invention. The following non-limiting examples are provided to further illustrate the present invention.

SPECIFIC EXAMPLES

All $^1$H NMR were recorded on a Bruker 300 MHz spectrometer. Low resolution mass spectra were obtained on an Agilent 1100 Series LC/MSD. Elemental analyses were performed by Robertson Microlit Laboratories (Madison, N.J.). The analytical HPLC utilized in the time course experiments was a Hewlett Packard Series 1050 with a Phenomenex C-18 column (30×4.6 mm, 3 μM). The mobile phase for the HPLC analyses was a gradient of water/acetonitrile with a 0.05% TFA additive.

The following examples describe the invention in greater detail and are intended to illustrate the invention, but not to limit it.

Preparative Scale Solution Phase Procedures

Example 1

N-Hydroxy-2-phenylacetamide. To methyl phenylacetate (0.288 mL, 2.0 mmol) in THF:MeOH: 50% aqueous NH$_2$OH (1:1:0.5, 2.5 mL) was added KCN (5 mg, 0.08 mmol, 4 mol %) and the mixture was stirred at ambient temperature. After 2 h the reaction was complete by HPLC. To the mixture was added saturated aqueous citric acid (25 mL) followed by extraction with EtOAc (3×25 mL). The organic phase was isolated, dried (MgSO$_4$), filtered, and the filtrate was concentrated in vacuo to give a residue. The residue was purified by reverse phase HPLC (C-18, 5μ 100×30 mm column), eluting with a gradient of acetonitrile:water (0.05% TFA). Following lyophilization of the product fractions there was obtained pure N-hydroxy-2-phenylacetamide as a fluffy solid (0.234 g, 77% yield): LRMS (M+H)$^+$: 152.1 m/z; $^1$H NMR (DMSO-d$_6$) δ: 10.6(s, 1H), 8.81(s, 1H), 7.2(m, 5H), 3.26(s, 2H); Anal (C,H,N): % C: (calc) 63.56; (found) 63.63; % H: (calc.) 6.00; (found) 5.91; % N: (calc.) 9.27, (found) 9.04.

Example 2

N-Hydroxy-3-phenylpropionamide. To methyl 3-phenyl propionate (0.328 g, 2.0 mmol) in THF:MeOH:50% aqueous NH$_2$OH (1:1:0.5, 2.5 mL) was added KCN (5 mg, 0.08 mmol, 4 mol %)) and the mixture was stirred at ambient temperature. After 3 h the reaction was complete by HPLC and saturated aqueous citric acid was added (25 mL) followed by extraction with EtOAc (3×25 mL). The organic phase was isolated, dried (MgSO$_4$), filtered, and the filtrate was concentrated in vacuo to give a residue. The residue was purified by reverse phase HPLC (C-18, 5μ 100×30 mm column), eluting with a gradient of acetonitrile: water (0.05% TFA). Following lyophilization of the product fractions there was obtained pure N-hydroxy-3-phenylpropionamide (IIc) as a fluffy solid (0.220 g, 67% yield): LRMS (M+H)$^+$: 166.0 m/z; $^1$H NMR (DMSO-d$_6$) δ: 10.31(s, 1H), 8.68(br, 1H), 7.17(m, 5H), 2.79(t, 2H), 2.21(t, 2H); Anal (C,H,N): % C (calc) 65.44, (found) 65.38; % H (calc.) 6.71, (found) 6.61; % N (calc.) 8.48, (found) 8.08.

Example 3

Solution Phase Time Course Experiments: Effect of KCN on the Conversion of Esters to Hydroxamic Acids Methyl 3-phenylpropionate to N-hydroxy-3-phenylpropionamide. Two batches of methyl 3-phenylpropionoate (0.10 g, 0.38 mmol) in 1:1 THF:MeOH (1 mL) were prepared. A portion of 50% aqueous NH$_2$OH (0.25 mL) was added to each batch followed by the immediate addition of KCN (5 mg, 0.08 mmol, 20 mol %) to one reaction while the other was maintained as a control. The parallel reactions were stirred at ambient temperature and 0.025 mL aliquots of each reaction mixture were withdrawn and diluted with 0.2 mL of MeOH at time points of 1, 2, 4, 6 and 24 h. The aliquots were analyzed by reverse phase HPLC within 10 min of being diluted. The ratio of starting ester methyl 3-phenylpropionate to product hydroxamic acid IIc was determined by reverse phase HPLC/MS and $^1$H NMR and also by HPLC retention times.

The effect of KCN as a promoter in the solution phase N-hydroxyamination of esters of Formula I was explored as described above. Reactions in which KCN was present (5 mg, 0.08 mmol, 20 mol %) were run in THF:MeOH with 50% aqueous hydroxylamine at room temperature (Table 1). In all cases, the addition of KCN accelerated the formation of the desired hydroxamic acid, product IIa–e. The conversion of methyl benzoate (Compound Ia, entry 1) to its corresponding hydroxamic acid is essentially complete after 24 h, while little of the corresponding hydroxamic acid IIa is formed in that same time in the absence of KCN. For entries 2, 3 and 4, almost all of the ester Compounds Ib–Id converted to their corresponding hydroxamic acid IIb–IId within 6 h in the presence of KCN, while considerable amounts of Ib–Id remain for the controls (where KCN is absent). In the case of Compound Ie (entry 5) the reaction is complete after 2 h with KCN while 60% of Ie is unchanged after 24 h in the absence of KCN. Trace amounts of the corresponding carboxylic acid are formed as a by-product in entries 2 and 3 (≦2%) with more substantial amounts of carboxylic acid formed for methyl benzoate (entry 1, 15%) and methyl mandelate (entry 4, 8%). No carboxylic acid was detected for the dihydroindole Ie (entry 5).

TABLE 1

Solution Phase Hydroxamic acid Formation from Esters with and without KCN additive

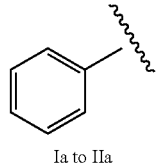

| | | | Ratio of Ester I: Hydroxamic Acid II | |
|---|---|---|---|---|
| Entry | $R^1$ | Time (h) | without KCN | with KCN |
| 1 | 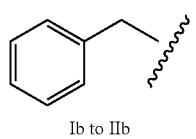<br>Ia to IIa | 1<br>2<br>4<br>6<br>24 | 100:0<br>100:0<br>99:1<br>97:3<br>95:5 | 86:14<br>76:24<br>56:44<br>43:57<br>4:96[b] |
| 2 | 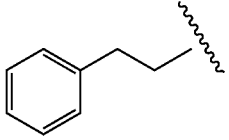<br>Ib to IIb | 1<br>2<br>4<br>6<br>24 | 94:6<br>89:11<br>78:22<br>65:35<br>48:52[c] | 21:79<br>9:91<br>1:99<br>0:100[c]<br>— |
| 3 | 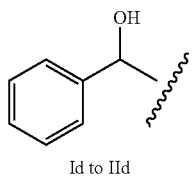<br>Ic to IIc | 1<br>2<br>4<br>6<br>24 | 82:18<br>73:27<br>62:38<br>58:42<br>38:62 | 41:59<br>17:83<br>4:96<br>2:98<br>2:98[c] |
| 4 | 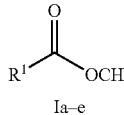<br>Id to IId | 1<br>2<br>4<br>6 | 87:13<br>82:18<br>65:35<br>57:43[d] | 4:96<br>1:99<br>0:100[d]<br>— |

TABLE 1-continued

Solution Phase Hydroxamic acid Formation from Esters with and without KCN additive

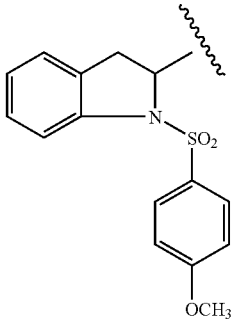

| | | | Ratio of Ester I: Hydroxamic Acid II | |
|---|---|---|---|---|
| Entry | $R^1$ | Time (h) | without KCN | with KCN |
| 5 | Ie to IIe | 2<br>24 | 90:10<br>60:40 | 0:100<br>— |

[a]Ratios were calculated from the integrated area for the ester or hydroxamic acid HPLC peaks divided by the total area for the ester and hydroxamic acid multiplied by 100.
[b]Final product contains about 15% carboxylic acid.
[c]Final product contains trace (<2%) carboxylic acid.
[d]Final product contains about 8% carboxylic acid.

Example 4

Evaluation of KCN on Reaction Profile

To five batches of methyl 3-phenylpropionoate (0.10 g, 0.38 mmol) in 1:1 THF:MeOH (1 mL) was added 50% aqueous $NH_2OH$ (0.25 mL). To four of the reactions KCN was added immediately in the following amounts: 1.2 mg (5 mol %), 2.5 mg (10 mol %), 5 mg (20 mol %) and 10 mg (40 mol %). One reaction was reserved as the control. The parallel reactions were stirred at ambient temperature and 0.025 mL aliquots of each reaction mixture was withdrawn and diluted with 0.2 mL of MeOH at time points of 1, 2, 4, 6 and 24 h. The aliquots were analyzed by reverse phase HPLC (214 nM) within 10 min of being diluted. Results are reported in FIG. 1.

FIG. 1. Effect of Increasing KCN mole concentration on the Rate of Conversion of Methyl 3-phenylpropionate to N-Hydroxy-3-phenylpropionamide.

As evidenced in FIG. 1, 20 mol % and 40 mol % of KCN proved to be the most efficient, while even relatively the low amounts of KCN additive, 5 mol % and 10 mol %, were better than the unassisted (0%) run. For synthetic scale reactions, smaller amounts of KCN were found to be the most convenient. The hydroxamic acids of methyl phenylacetate Ib and methyl 3-phenylpropionate Ic were prepared on a 2 mmol scale using a mixture of THF:MeOH:50% aqueous $NH_2OH$ (1:1:0.5, 2.5 mL) with KCN (5 mg, 0.08 mmol, 4 mol %). A 77% yield of the hydroxamic acid IIb was obtained from Ib after 2 h at ambient temperature and a 67% yield of the hydroxamic acid IIc from Ic after 3 h at ambient temperature.

Example 5

Solid Phase Preparative Scale Procedure

Hydroxamic acid of N-(4-methoxyphenylsulfonyl)-DL-phenylalanine. To N-(4-methoxyphenylsulfonyl)-DL-phenylalanine bound to hydroxymethylbenzamide (HMBA-AM) resin supplied by Calbiochem-Novabiochem Bad Soden, Germany (0.20 g of modified resin with a loading of 1 mmol of compound to 1 g of resin, 0.20 mmol) in THF:MeOH:50% aqueous $NH_2OH$ (1:1:0.4, 2.4 mL) was added KCN (5 mg, 0.08 mmol, 40 mol %). The reaction was shaken at ambient temperature for 4 h, then the resin was filtered, washed with MeOH and the solution was evaporated with a stream of Argon gas. The residue was purified by reverse phase HPLC (C-18, 5μ 100×30 mm column) by elution with a gradient of acetonitrile: water (0.05% TFA). Following lyophilization of the product fractions there was obtained the pure hydroxamic acid of N-(4-methoxyphenylsulfonyl)-DL-phenylalanine (0.040 g, 0.11 mmol, 57% yield): LRMS $(M+H)^+$: 351.0 m/z; $^1H$ NMR (DMSO-$d_6$) δ: 10.5(s, 1H), 8.80(br, 1H), 8.00(d, 1H), 7.47(d, 2H), 7.15(m, 3H), 7.05(m, 2H), 6.89(d, 2H), 3.78(s, 3H), 3.69(dd, 1H), 2.76(dd, 1H), 2.52(dd, 1H); Anal (C,H,N): % C: (calc.) 54.84, (found) 54.56; % H: (calc.) 5.18; (found) 4.88; % N: (calc.) 7.99, (found) 7.59.

Example 6

Solid Phase Preparative Scale Procedure

To explore the effectiveness of cyanide in the assistance of hydroxylamine mediated cleavage for solid phase library synthesis, hydroxymethylbenzamide (HMBA-AM) resin was chosen for the well-established compatibility between the ester linkage and Fmoc- and Boc-chemistry, and its stability towards Mitsunobu and reductive amination conditions. A solid phase library of DL-phenylalanine and several constrained analogs (AAa–c, Scheme 3) was prepared on the HMBA resin by the esterification of the Fmoc protected DL-aminoacids using standard DCC coupling conditions overnight. The resin-bound Fmoc aminoacids BBa–c were deprotected with piperidine-DMF (1:4) and sulfonated with 4-methoxybenzenesulfonyl chloride to give Compounds IIIa–c. In this instance, the optimal reaction conditions for cleavage from the resin of the sulfonamide esters to yield the free hydroxamic acids (IVa–c, Table 2) were 5:5:2 THF:MeOH:50% aqueous $NH_2OH$ and 5 mg (0.08 mmol, 40 to 80 mol %) of KCN for 100 to 200 mg of loaded resin.

The importance of KCN additive using these conditions was assessed with this series of analogs by following the time-dependant cleavage of the substrates from the solid support by hydroxylamine in parallel experiments with and without KCN (Table 2). In the case of entries 1 and 2, KCN assisted cleavage to the hydroxamic acid is complete after 2 hours, while in the unassisted parallel experiments, up to 20 h or more for entries 1 and 2 are required. For entry 3, the KCN assisted experiment is complete after 2 hours while the unassisted cleavage from the resin to the hydroxamic acid is complete in 4 hours. It was important to follow these reactions carefully and work up them upon completion. Extended exposure to the hydroxylamine solution appeared to result in decomposition of the product.

Scheme 3. Preparation of the Solid Phase Library.

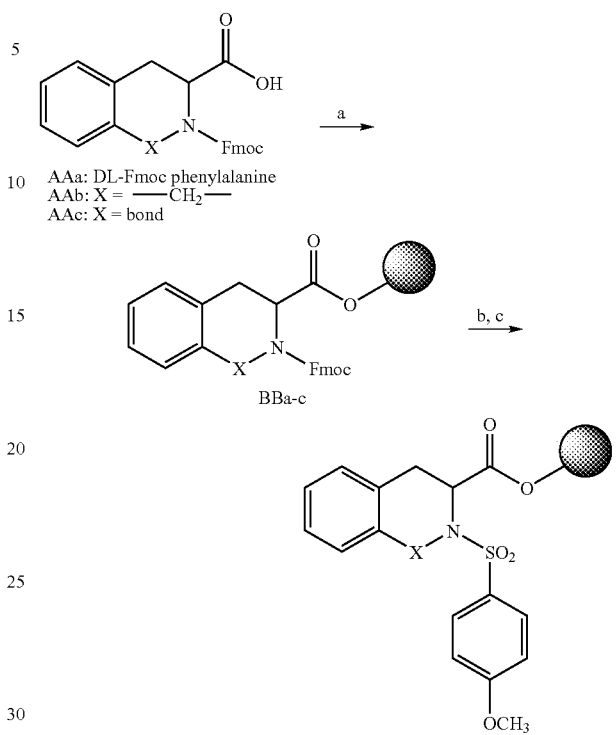

AAa: DL-Fmoc phenylalanine
AAb: X = —$CH_2$—
AAc: X = bond

Reagents and conditions: (a), AAa-c (3 eq.), HMBA-AM resin, DCC (3eq.), DMAP(3eq.), DMF, rt, 15 h; (b) piperidine-DMF 1:4; (c), 4-MeOPhSO$_2$Cl (3eq.), Et$_3$N (3eq.), DCM, rt, 3h;

To demonstrate the utility of this procedure on a synthetic scale, 200 mg of the resin IIIa (0.2 mmol of compound based on a loading capacity of 1 mmol of compound per 1 g of HMBA-AM resin) was treated with a mixture of THF:MeOH:50% aqueous $NH_2OH$ (1:1:0.4, 2.4 mL) and KCN (5 mg, 40 mol %) to give a 57% yield of hydroxamic acid IVa, based upon the presumed resin loading.

Example 7

Procedure for Solid Phase Resin Cleavage Time Course Experiments

Cleavage of N-(4-methoxyphenylsulphonyl)-DL-phenylalanine modified HMBA-AM resin (IIIa) to the hydroxamic acid IVa (Entry 1).

Stock Solution Preparation

Indan-1-ol (33 mg) was dissolved with a mixture of THF (5 mL):MeOH (5 mL):$NH_4OH$ (1 mL, 50% aqueous solution).

Resin Cleavage

THF (0.3 mL) and the stock solution (1 mL) prepared above were added to resin IIIa (100 mg, estimated at 0.1 mmol based upon theoretical resin loading) and the reaction was shaken. For the reaction with KCN, 5 mg of KCN (0.08 mmol, 80 mol %) was added immediately while, for the control, no KCN was added. At time points of 0.5, 1, 2, 4, 6 and 24 h an aliquot (0.05 mL) of the reaction was removed by syringe and immediately diluted with MeOH (0.20 mL). These samples were analyzed by HPLC within 10 min of sampling. The absorbance of the 1-indanol peak and the product IVa were recorded for each time point. For details on product peak identification and the data used to estimate the percent conversion to product see the Supplemental Material section.

TABLE 2

Solid Phase Reaction of Hydroxylamine with Esters of HMBA-AM Resin IIIa-c with and without KCN additive.

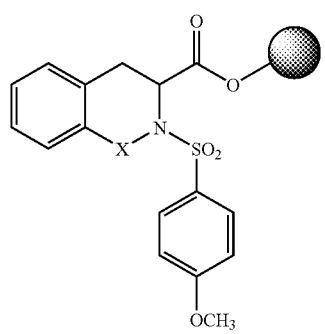

THF/MeOH/
NH₂OH (50% aqueous) 5:5:2

IIIa N-(4-methoxyphenyl)sulphonyl-DL-phenylalanine
IIIb: X = —CH₂—
IIIc: X = bond TABLE 2-continued Solid Phase Reaction of Hydroxylamine with Esters of HMBA-AM Resin IIIa-c with and without KCN additive.

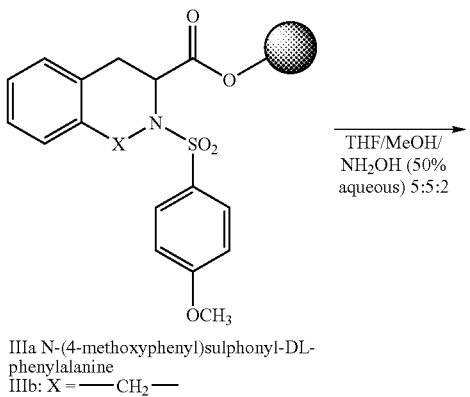

THF/MeOH/
NH₂OH (50% aqueous) 5:5:2

IIIa N-(4-methoxyphenyl)sulphonyl-DL-phenylalanine
IIIb: X = —CH₂—
IIIc: X = bond

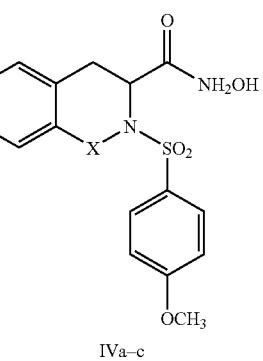

IVa–c

| Entry | Products IVa–c | Time (h) | % Conversion[a] to IV without KCN | % Conversion[a] to IV with KCN |
|---|---|---|---|---|
| 1 | IVa | 0.5 | 1.5 | 58 |
|   |   | 1 | 3 | 83 |
|   |   | 2 | 5.8 | 100 |
|   |   | 4 | 11.9 | — |
|   |   | 6 | 16 | — |
|   |   | 20 | 28 | — |
| 2 | IVb | 0.5 | 6.5 | 68 |
|   |   | 1 | 12 | 100 |
|   |   | 2 | 16 | — |
|   |   | 4 | 45 | — |
|   |   | 20 | 100 | — |

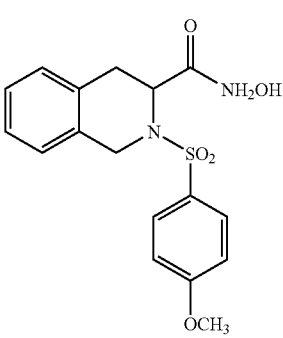

IVb

TABLE 2-continued

Solid Phase Reaction of Hydroxylamine with Esters of HMBA-AM Resin IIIa-c with and without KCN additive.

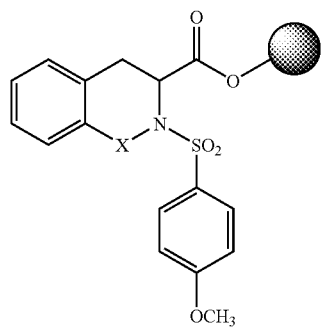

IIIa N-(4-methoxyphenyl)sulphonyl-DL-phenylalanine
IIIb: X = —CH₂—
IIIc: X = bond

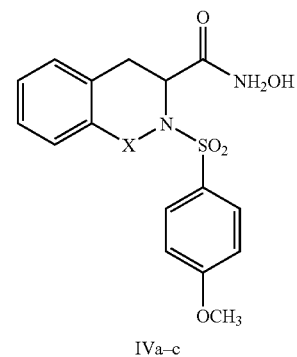

IVa–c

| Entry | Products Iva–c | Time (h) | % Conversion[a] to IV without KCN | with KCN |
|---|---|---|---|---|
| 3 | 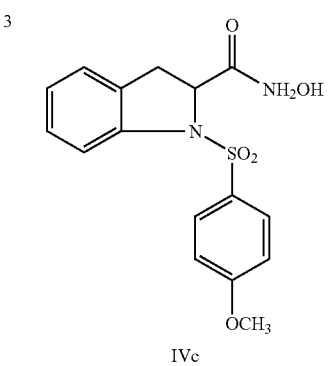 IVc | 0.5 | 18 | 85 |
| | | 1 | 34 | 85 |
| | | 2 | 56 | 100 |
| | | 4 | 100 | — |
| | | 20 | — | — |

[a]Determination of '% Conversion': The HPLC peak areas of products IVa–c were normalized to the peak area of an internal standard (1-indanol). Complete cleavage of the product was apparent when the normalized peak areas for IVa–c were observed to increase no further at subsequent time points. Percentages of conversion were all calculated relative to time point at which complete cleavage was observed.

TABLE 2-continued

Solid Phase Reaction of Hydroxylamine with Esters of HMBA-AM Resin IIIa-c with and without KCN additive.

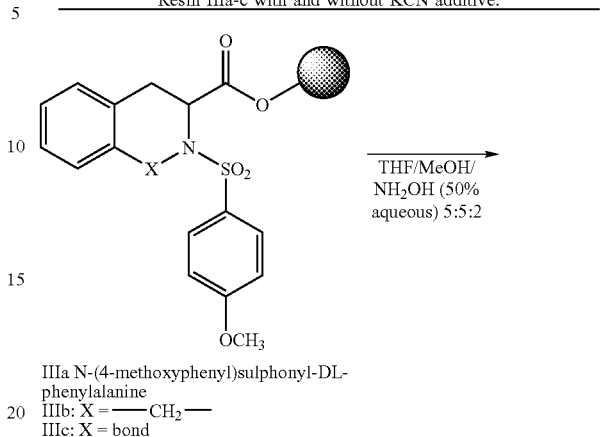

IIIa N-(4-methoxyphenyl)sulphonyl-DL-phenylalanine
IIIb: X = —CH₂—
IIIc: X = bond

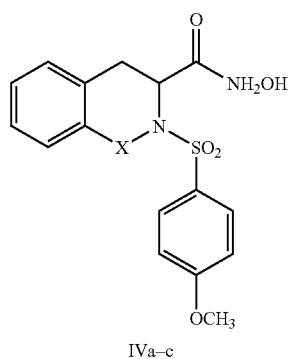

IVa–c

| Entry | Products Iva–c | Time (h) | % Conversion[a] to IV without KCN | with KCN |
|---|---|---|---|---|

[b]In these experiments 5 mg (0.08 mmol, 80 mol %) of KCN was used for 100 mg of resin.

We claim:

1. A process for synthesizing hydroxamic acids, comprising reacting under suitable conditions an ester with hydroxylamine in the presence of cyanide anion in an organic solvent.

2. The process of claim 1 wherein the hydroxylamine is from about 20 to about –80 percent by weight aqueous hydroxylamine.

3. The process of claim 1 wherein the organic solvent is selected from the group consisting of methanol, ethanol, methanol/tetrahydrofuran and methanol/DMF.

4. The process of claim 3 wherein the organic solvent is selected from the group consisting of methanol and ethanol.

5. The process of claim 1 wherein the cyanide salt is present in from about 5 to about 50 mole percent.

6. The process of claim 5 wherein the cyanide salt is present in from about 20 to about 40 mole percent.

7. The process of claim 1 wherein the temperature is in the range of from about 0 to about 100° C.

8. The process of claim 7 wherein the temperature is about 25° C.

* * * * *